(12) United States Patent
Cao et al.

(10) Patent No.: US 12,029,599 B2
(45) Date of Patent: Jul. 9, 2024

(54) MAMMOGRAPHY IMAGING SYSTEM USING X-RAY FLUORESCENCE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 264 days.

(21) Appl. No.: 17/859,499

(22) Filed: Jul. 7, 2022

(65) Prior Publication Data
US 2022/0330910 A1    Oct. 20, 2022

Related U.S. Application Data

(63) Continuation of application No. PCT/CN2020/076789, filed on Feb. 26, 2020.

(51) Int. Cl.
*A61B 6/00* (2024.01)
*A61B 6/04* (2006.01)
(Continued)

(52) U.S. Cl.
CPC ............ *A61B 6/482* (2013.01); *A61B 6/0414* (2013.01); *A61B 6/4241* (2013.01); *A61B 6/485* (2013.01);
(Continued)

(58) Field of Classification Search
None
See application file for complete search history.

(56) References Cited

U.S. PATENT DOCUMENTS

2005/0288581 A1* 12/2005 Kapur .................. A61B 8/4281
                                                                128/915
2006/0182217 A1  8/2006 Harding et al.
(Continued)

FOREIGN PATENT DOCUMENTS

CN       1926574 A       3/2007
CN     101410726 A       4/2009
(Continued)

OTHER PUBLICATIONS

Ren, Liqiang, et al. "Three dimensional x ray fluorescence mapping of a gold nanoparticle loaded phantom." Medical physics 41.3 (2014): 031902.
(Continued)

*Primary Examiner* — David P Porta
*Assistant Examiner* — Carolyn Fin
(74) *Attorney, Agent, or Firm* — IPRO, PLLC; Qian Gu

(57) ABSTRACT

Disclosed herein is a system comprising: a radiation source configured to cause emission of characteristic X-rays of a chemical element in human breast tissues by generating and directing radiation to the human breast tissues; a first image sensor configured to capture a first set of images of the human breast tissues using the characteristic X-rays; a second image sensor configured to capture a second set of images of the human breast tissues using the radiation that has transmitted through the human breast tissues; and a clamp configured to compress the human breast tissues against the second image sensor; wherein the first image sensor is between the clamp and the second image sensor.

22 Claims, 17 Drawing Sheets

(51) Int. Cl.
  *A61B 6/42*   (2024.01)
  *A61B 6/50*   (2024.01)
  *G01N 23/2206*  (2018.01)
  *G01N 23/223*  (2006.01)

(52) U.S. Cl.
  CPC ......... *A61B 6/502* (2013.01); *G01N 23/2206* (2013.01); *G01N 23/223* (2013.01); *A61B 6/4208* (2013.01); *A61B 6/5235* (2013.01)

(56) References Cited

U.S. PATENT DOCUMENTS

| | | | |
|---|---|---|---|
| 2008/0086059 A1* | 4/2008 | Keppel | A61B 90/17 600/562 |
| 2014/0180082 A1* | 6/2014 | Evans | A61B 6/502 600/436 |
| 2019/0056338 A1 | 2/2019 | Li et al. | |
| 2020/0009402 A1 | 1/2020 | Silver | |

FOREIGN PATENT DOCUMENTS

| | | |
|---|---|---|
| CN | 101646449 A | 2/2010 |
| CN | 105520742 A | 4/2016 |
| CN | 106999134 B | 11/2020 |
| DE | 10332301 B4 | 7/2009 |

OTHER PUBLICATIONS

Hayashi, Yasuhiko, and Fumio Okuyama. "New approach to breast tumor detection based on fluorescence x-ray analysis." GMS German Medical Science 8 (2010).

\* cited by examiner

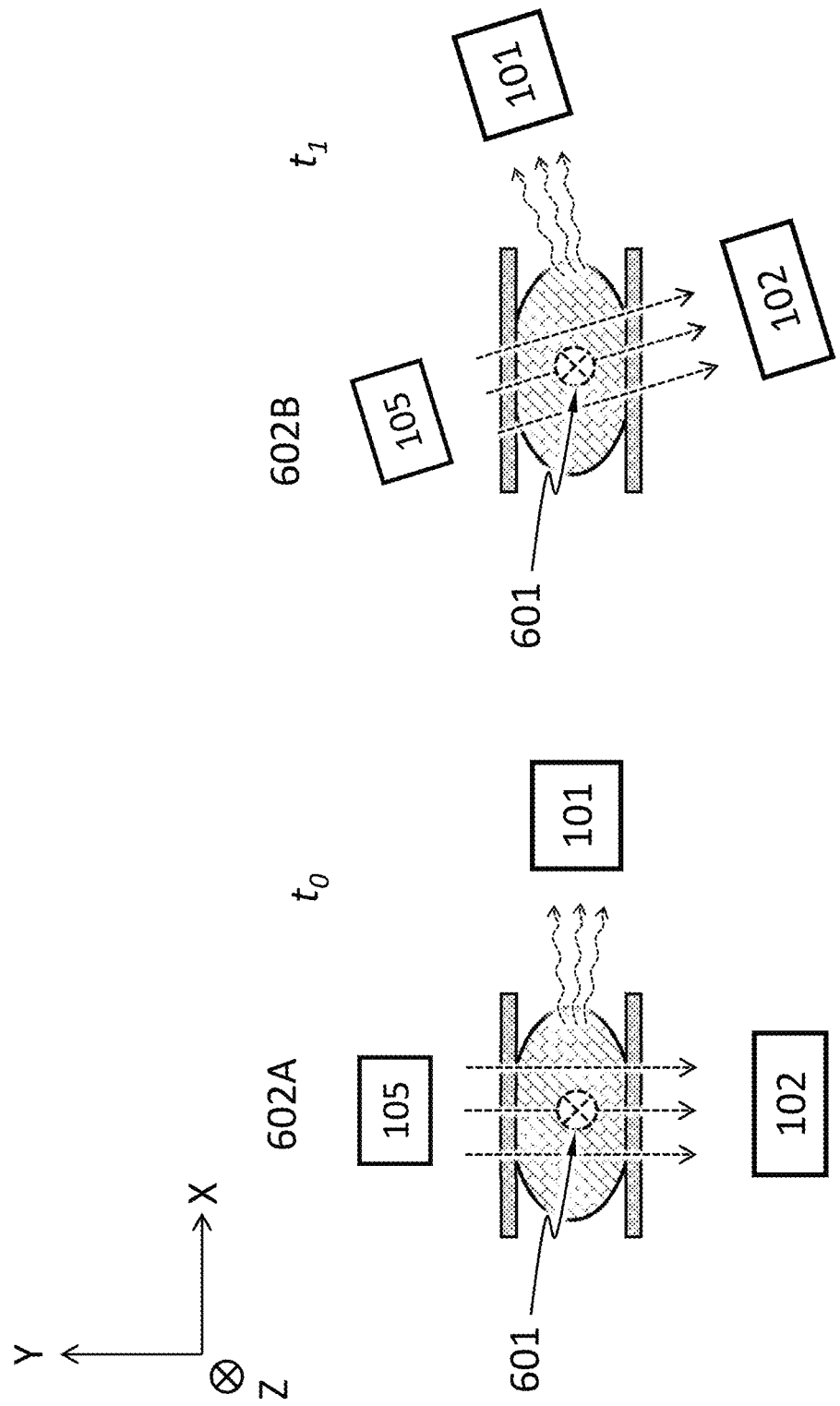

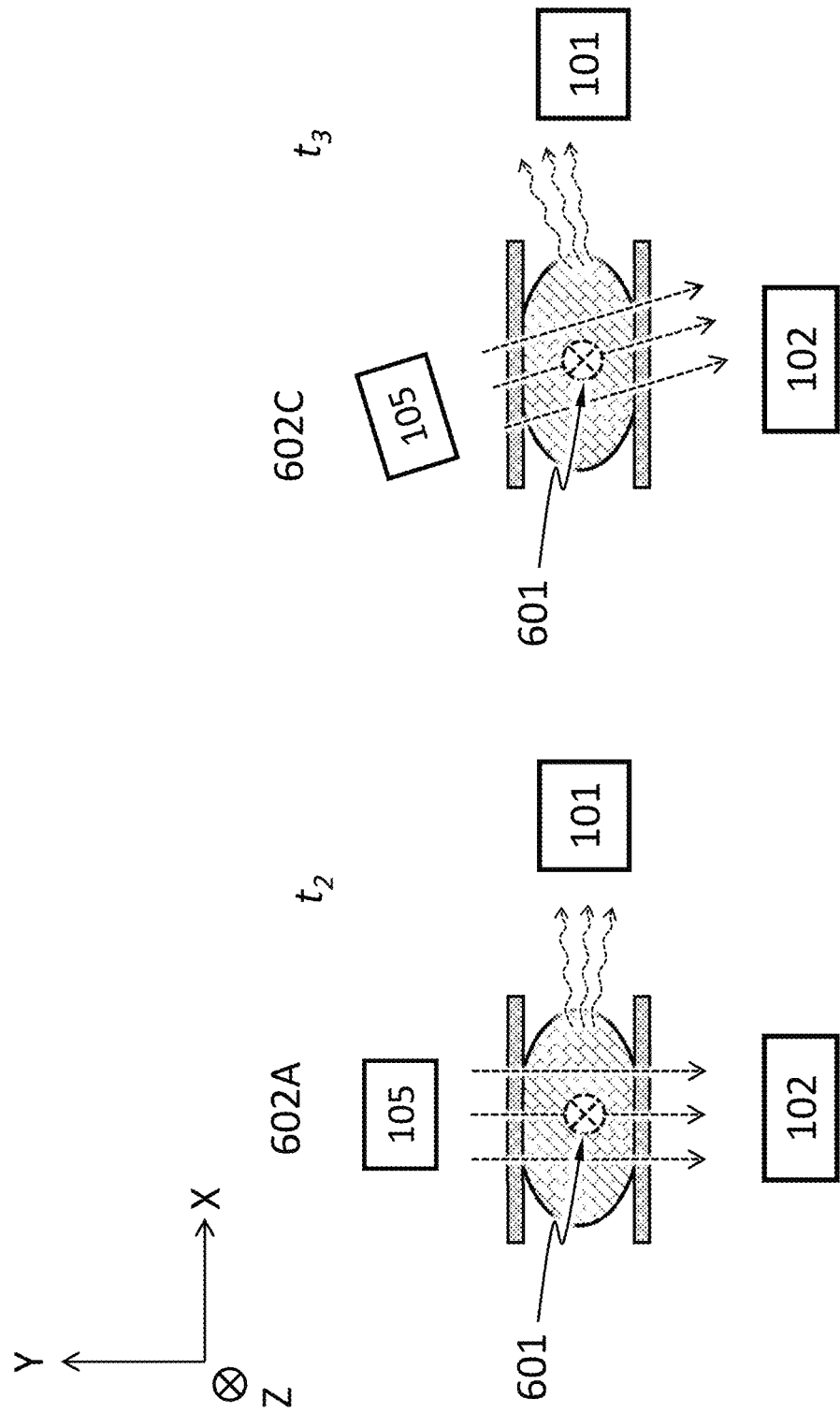

MAMMOGRAPHY IMAGING SYSTEM USING X-RAY FLUORESCENCE

BACKGROUND

X-ray fluorescence (XRF) is the emission of characteristic X-rays from a material that has been excited by, for example, exposure to high-energy X-rays or gamma rays. An electron on an inner orbital of an atom may be ejected, leaving a vacancy on the inner orbital, if the atom is exposed to X-rays or gamma rays with photon energy greater than the ionization potential of the electron. When an electron on an outer orbital of the atom relaxes to fill the vacancy on the inner orbital, an X-ray (fluorescent X-ray or secondary X-ray) is emitted. The emitted X-ray has a photon energy equal the energy difference between the outer orbital and inner orbital electrons.

For a given atom, the number of possible relaxations is limited. As shown in FIG. 1A, when an electron on the L orbital relaxes to fill a vacancy on the K orbital (L→K), the fluorescent X-ray is called Kα. The fluorescent X-ray from M→K relaxation is called Kβ. As shown in FIG. 1B, the fluorescent X-ray from M→L relaxation is called Lα, and so on.

SUMMARY

Disclosed herein is a system comprising: a radiation source configured to cause emission of characteristic X-rays of a chemical element in human breast tissues by generating and directing radiation to the human breast tissues; a first image sensor configured to capture a first set of images of the human breast tissues using the characteristic X-rays; a second image sensor configured to capture a second set of images of the human breast tissues using the radiation that has transmitted through the human breast tissues; and a clamp configured to compress the human breast tissues against the second image sensor; wherein the first image sensor is between the clamp and the second image sensor.

In an aspect, the radiation source comprises a filter configured to block radiation not having sufficient energy to cause the emission of the characteristic X-rays.

In an aspect, the chemical element is rhenium or iodine.

In an aspect, the chemical element is not radioactive.

In an aspect, the chemical element is bound to a ligand.

In an aspect, the first image sensor comprises an array of pixels, and is configured to count numbers of photons of the characteristic X-rays incident on the pixels within a period of time.

In an aspect, the first image sensor comprises an X-ray absorption layer comprising GaAs.

In an aspect, the first image sensor does not comprise a scintillator.

In an aspect, the first set of images are captured using only the characteristic X-rays.

In an aspect, the system further comprises a processor configured to determine a three-dimensional distribution of the chemical element, based on the first set of images.

In an aspect, the processor is configured to reconstruct a three-dimensional image of the human breast tissues based on the second set of images.

In an aspect, the processor is configured to superposing the three-dimensional distribution of the chemical element and the three-dimensional image.

In an aspect, the first image sensor is configured to move between a first position relative to the radiation source and a second position relative to the radiation source.

In an aspect, the first image sensor, the second image sensor and the radiation source are configured to collectively rotate relative to the human breast tissues.

In an aspect, the radiation source is configured to rotate relative to the human breast tissues while the first image sensor and the second image sensor remain stationary relative to the human breast tissues.

Disclosed herein is a method, comprising: causing emission of characteristic X-rays of a chemical element in human breast tissues by directing radiation to the human breast tissues; capturing a first set of images of the human breast tissues using the characteristic X-rays using a first image sensor; capturing a second set of images of the human breast tissues using the radiation that has transmitted through the human breast tissues using a second image sensor; determining a three-dimensional distribution of the chemical element in the human breast tissues based on the first set of images; reconstructing a three-dimensional image of the human breast tissues based on the second set of images; superposing the three-dimensional distribution of the chemical element and the three-dimensional image; wherein the human breast tissues are compressed by a clamp against the second image sensor; wherein the first image sensor is between the clamp and the second image sensor.

In an aspect, the chemical element is rhenium or iodine.

In an aspect, the chemical element is not radioactive.

In an aspect, the chemical element is bound to a ligand.

In an aspect, the first image sensor comprises an array of pixels, and is configured to count numbers of photons of the characteristic X-rays incident on the pixels within a period of time.

In an aspect, capturing the first set of images are captured using only the characteristic X-rays.

In an aspect, the first image sensor and the second image sensor remain stationary relative to the human breast tissues during capturing the first set of images and capturing the second set of images.

BRIEF DESCRIPTION OF FIGURES

FIG. 7A-FIG. 7B schematically show movements of the first image sensor, the second image sensor and the radiation source relative to the human breast tissues, according to an embodiment.

FIG. 7C-FIG. 7D schematically show movements of the radiation source relative to the human breast tissues, according to an embodiment.

DETAILED DESCRIPTION

Figure 1A:
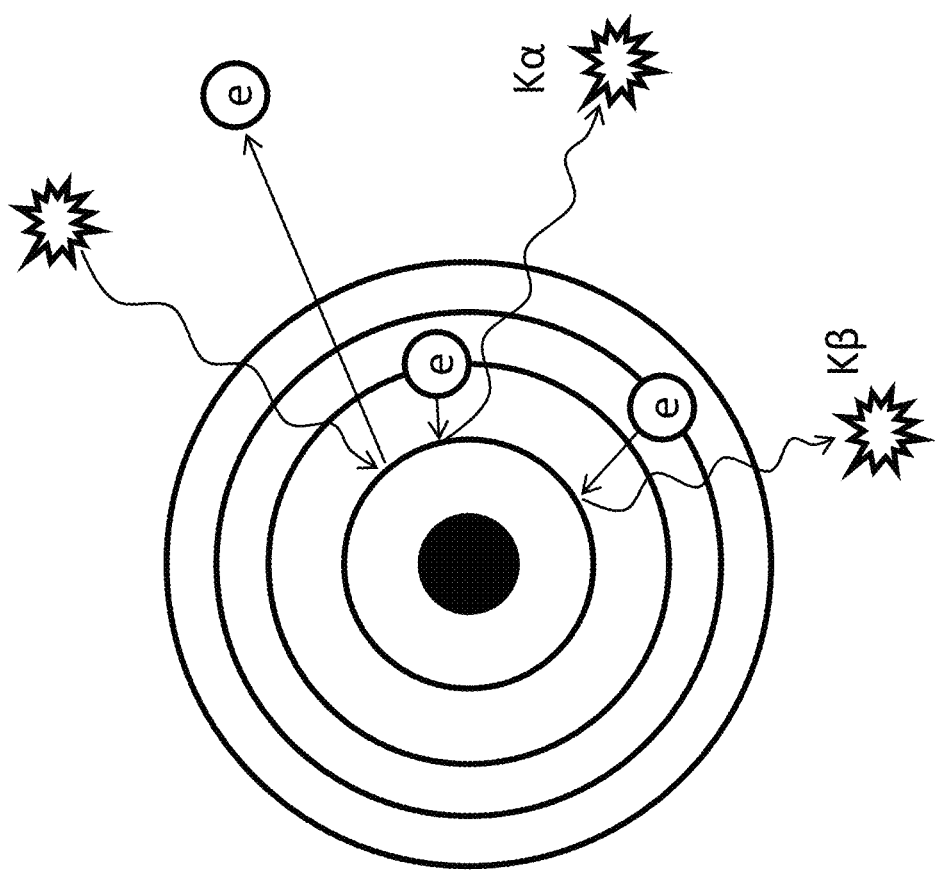
FIG. 1A and FIG. 1B schematically show mechanisms of XRF.
Figure 1B:
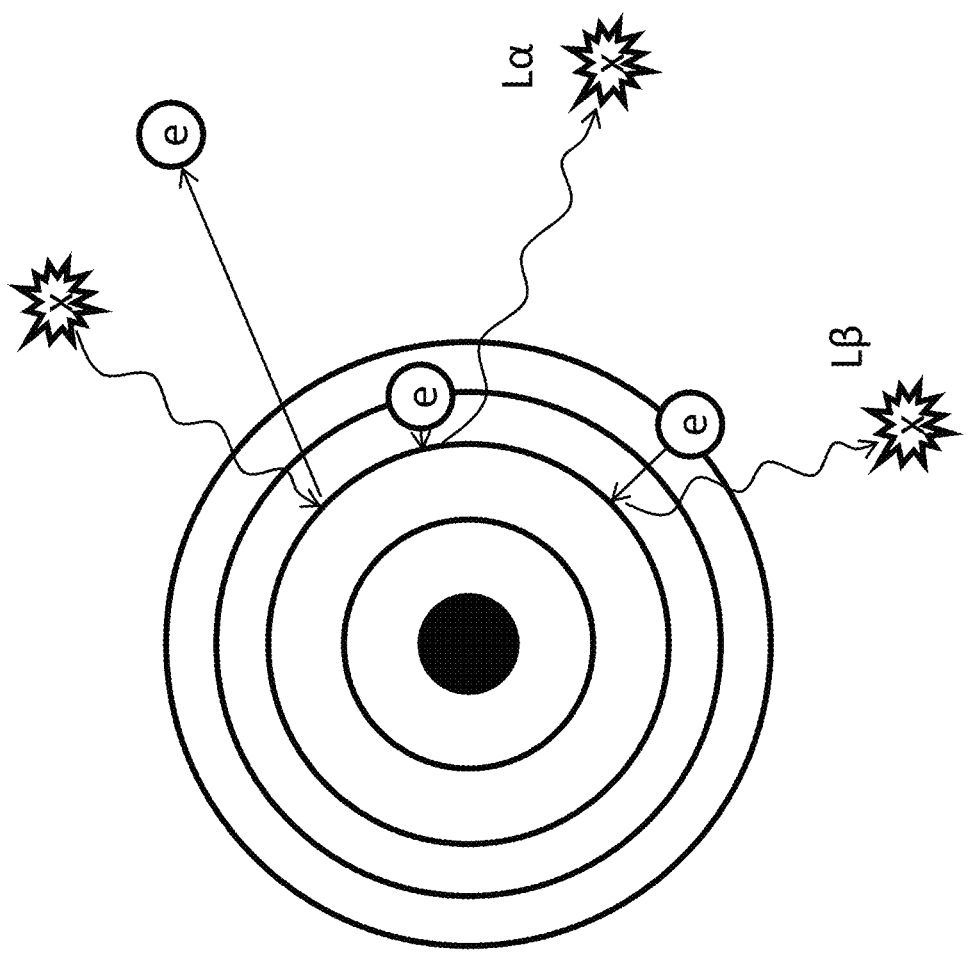
Figure 2:
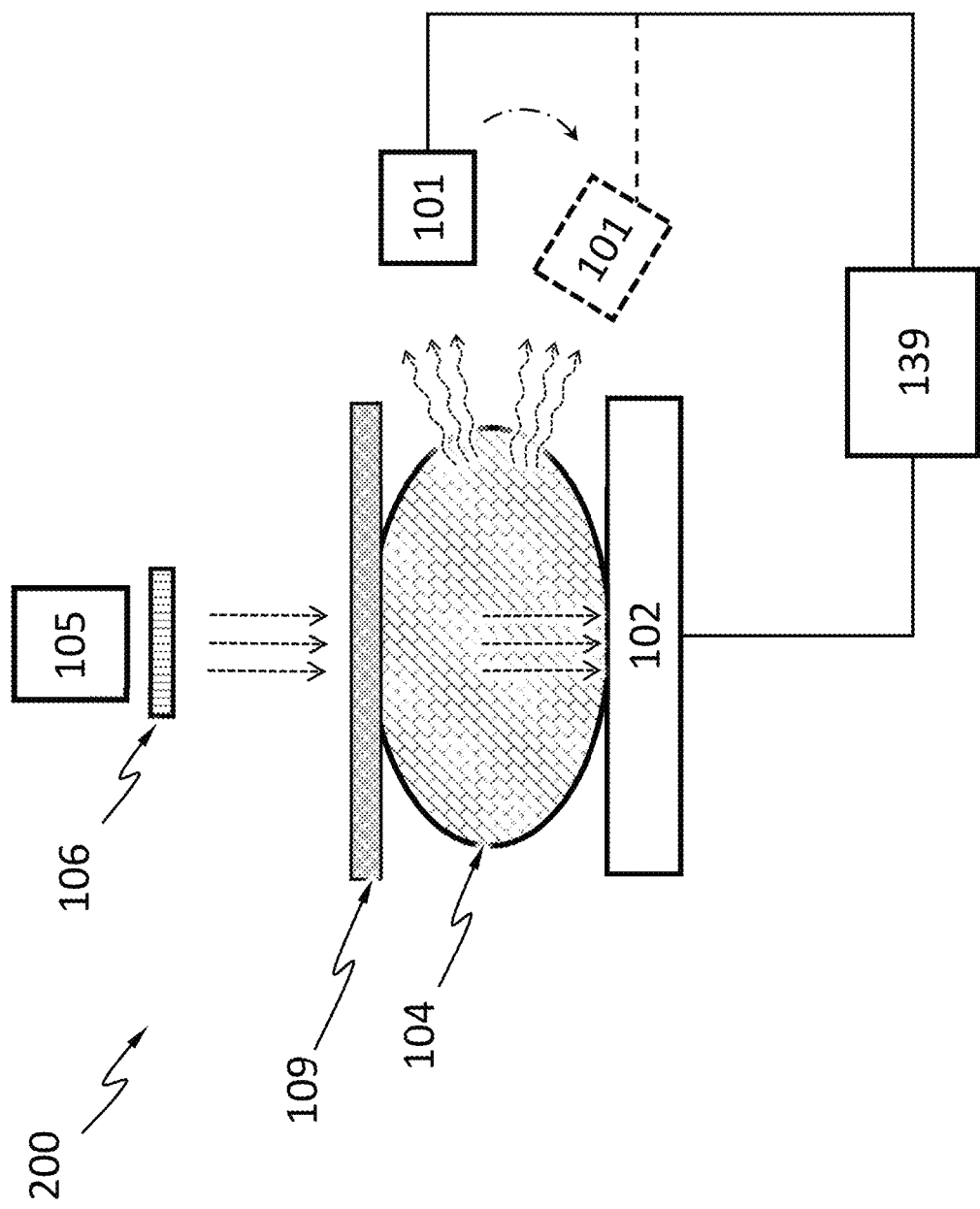
FIG. 2 schematically shows a system, according to an embodiment.

FIG. 2 schematically shows a system 200 comprising a first image sensor 101, a second image sensor 102 and a radiation source 105, according to an embodiment. The first image sensor 101 and the second image sensor 102 and the radiation source 105 may be positioned at or moved to multiple positions relative to an object (e.g., human breast tissues 104 as shown in FIG. 2). For example, the first image sensor 101, the second image sensor 102 and the radiation source 105 may be movable towards and away from the human breast tissues 104 or may be rotatable relative to the human breast tissues 104. Relative positions between the first image sensor 101, the second image sensor 102, and the radiation source 105 may or may not be fixed during the movement or the rotation. The first image sensor 101, the second image sensor 102 may be arranged at about the same distance or different distances from the human breast tissues 104. Other suitable arrangement of the first image sensor 101, the second image sensor 102 may be possible. The first image sensor 101, the second image sensor 102 may be spaced equally or unequally apart in the angular direction. In an embodiment, the first image sensor 101 does not include a scintillator.

The system 200 may include more than one radiation source 105. In one embodiment, the radiation source 105 irradiates the human breast tissues 104 with radiation that can cause a chemical element (e.g., rhenium, or iodine) to emit characteristic X-rays (e.g., by fluorescence). The chemical element may be introduced into the human breast tissues 104 orally in pills or liquids, or by injection. In an example, the chemical element is not radioactive. The chemical element may be bound to a ligand. The radiation source 105 may further include a filter 106, which is configured to block radiation that does not have sufficient energy to cause the emission of the characteristic X-rays from reaching the human breast tissues 104. The radiation source 105 may be movable or stationary relative to the human breast tissues 104.

In an embodiment, the first image sensor 101 captures a first set of images of the human breast tissues 104 using only the characteristic X-rays of the chemical element in the human breast tissues (e.g., by detecting the intensity distribution of the characteristic X-rays). Namely, the first image sensor 101 may disregard any radiation other than the characteristic X-rays. In one embodiment, the human breast tissues 104 are compressed by a clamp 109 against the second image sensor 102. The human breast tissues 104 do not have to be in direct physical contact with the second image sensor 102. The clamp 109 may include a material that has a low mass attenuation coefficient for the radiation from the radiation source 105. As shown in FIG. 2, the first image sensor 101 may be at positions between the clamp 109 and the second image sensor 102 where they may receive radiation from the radiation source 105 that has transmitted through the human breast tissues 104. The first image sensor 101 may be movable or stationary relative to the human breast tissues 104.

In an embodiment, the second image sensor 102 captures a second set of images of the human breast tissues 104 using radiation that has transmitted through the human breast tissues 104, as shown in FIG. 2. The second image sensor 102 may be movable or stationary relative to the human breast tissues 104.

In an embodiment, the chemical element is not radioactive and is introduced into the human body and absorbed by the human breast tissues 104. When the radiation from the radiation source 105 is directed toward the human breast tissues 104, the non-radioactive chemical element inside the human breast tissues 104 may be excited by the radiation and emit the characteristic X-rays. The characteristic X-rays may include the K lines, or the K lines and the L lines. The first set of images of the human breast tissues 104 may be captured with the characteristic X-rays by the first image sensor 101. The first set of images may include images captured when the first image sensor 101 is at multiple locations relative to the human breast tissues 104. The first image sensor 101 may disregard X-rays with energies different from the characteristic X-rays of the chemical element. A three-dimensional distribution of the chemical element inside the human breast tissues 104 may be determined by a processor 139, based on the first set of images. The second set of images of the human breast tissues 104 may be captured using radiation from the radiation source 105 and transmitted through the human breast tissues 104 by the second image sensor 102. The set of images may include images captured when the second image sensor 102 is at multiple locations relative to the human breast tissues 104. A three-dimensional distribution of the human breast tissues 104 may be reconstructed by the processor 139, based on the second set of images. The processor 139 may be further configured to superpose the three-dimensional distribution of the chemical element and the three-dimensional image of the human breast tissues 104.

Figure 3A:
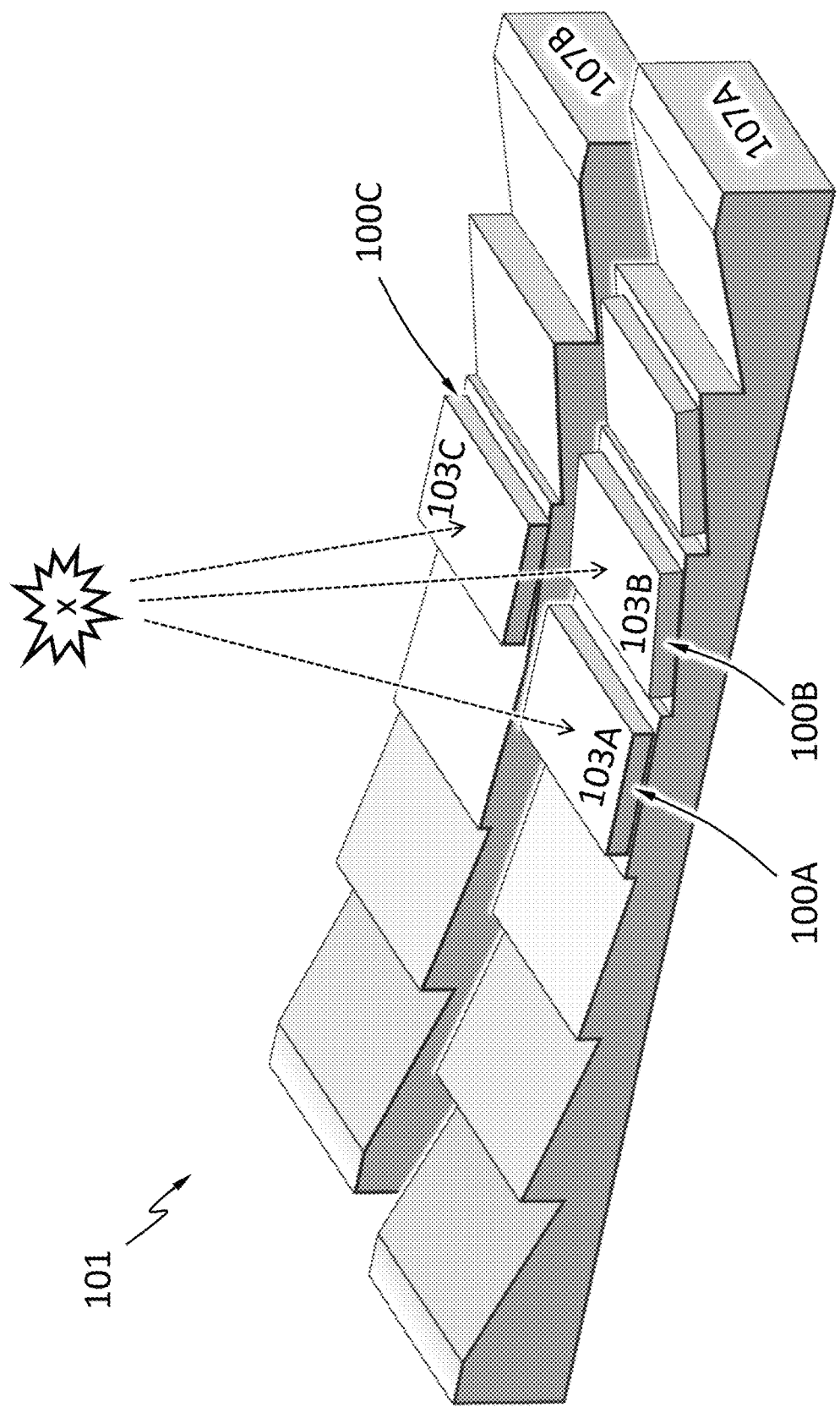
FIG. 3A and FIG. 3B schematically show a perspective view of a first image sensor comprising a plurality of X-ray detectors, according to an embodiment.

FIG. 3A schematically shows a perspective view of the first image sensor 101 comprising a plurality of X-ray detectors 100 (e.g., a first X-ray detector 100A, a second X-ray detector 100B, a third X-ray detector 100C in FIG. 3A), according to an embodiment. For brevity, only three X-ray detectors are shown in FIG. 3A but the first image sensor 101 may have many more X-ray detectors. Each of the X-ray detectors 100 may comprise a planar surface configured to receive characteristic X-rays emitted from the human breast tissues 104. Namely, the first X-ray detector 100A may have a planar surface 103A configured to receive characteristic X-rays, the second X-ray detector 100B may have a planar surface 103B, the third X-ray detector 100C may have a planar surface 103C, respectively. In one embodiment, the planar surfaces (e.g. 103A and 103B) of the first X-ray detector 100A and the second X-ray detector 100B are not parallel, the planar surfaces (e.g. 103B and 103C) of the second X-ray detector 100B and the third X-ray detector 100C are not parallel, and the planar surfaces (e.g. 103C and 103A) of the third X-ray detector 100C and the first X-ray detector 100A are not parallel.

In one embodiment, the plurality of X-ray detectors 100 are arranged on a plurality of supports 107 (e.g. a first support 107A, a second support 107B), according to an embodiment. FIG. 3A shows that the first X-ray detector 100A and the second X-ray detector 100B are mounted on the first support 107A, and that the third X-ray detector 100C is mounted on the second support 107B. In the example of FIG. 3A, the first X-ray detector 100A, the second X-ray detector 100B, and the third X-ray detector 100C are not arranged in the same row.

Figure 3B:
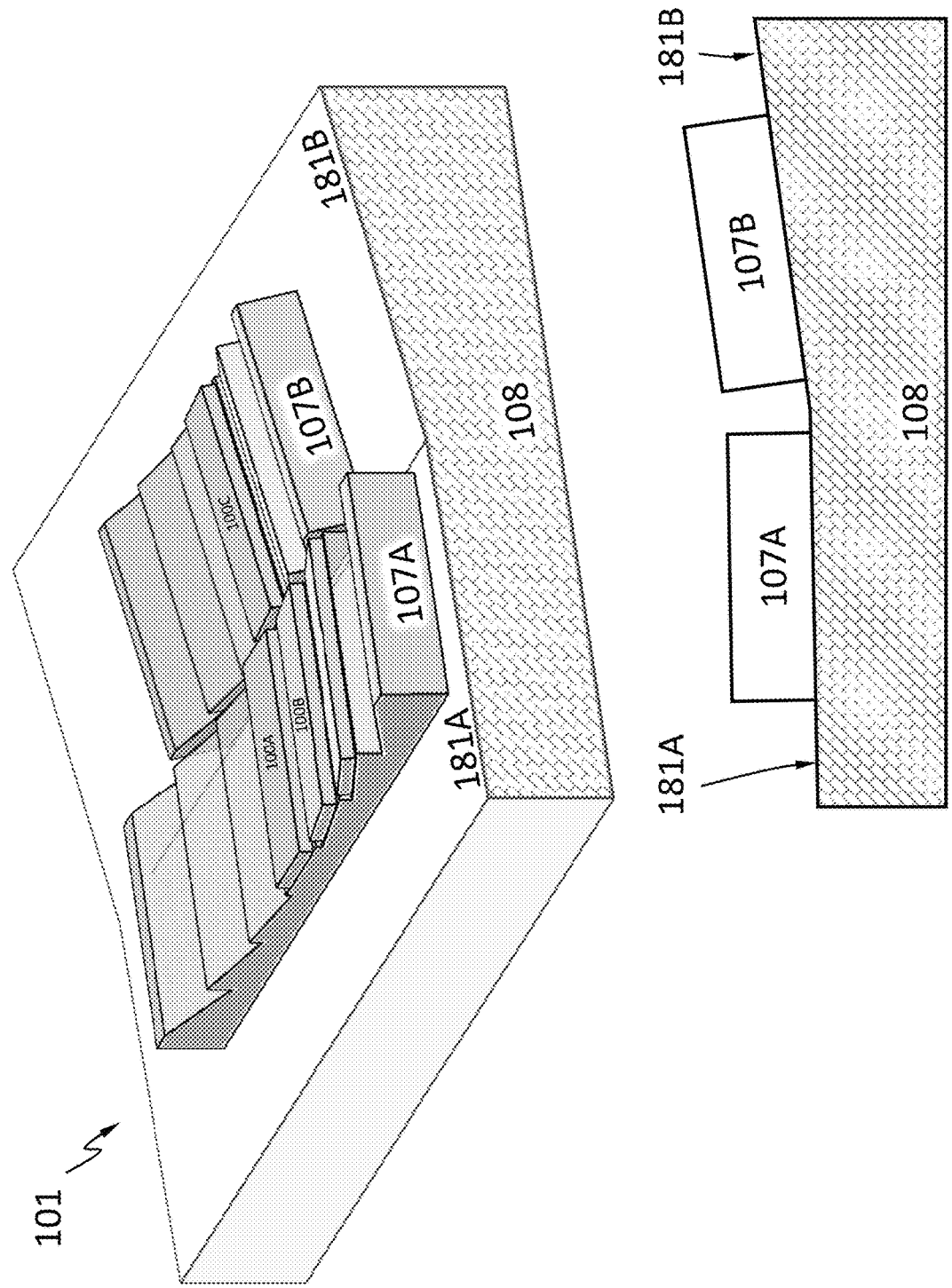

The first support 107A and the second support 107B may not be directly joined together, according to an embodiment. The first support 107A and the second support 107B may be mounted to a system support 108, as the example schematically shows in FIG. 3B. The system support 108 may include multiple mutually unparallel faces (e.g., 181A, 181B). The first support 107A is mounted to a first face 181A of the system support 108, the second support 107B is mounted to a second face 181B, such that the first support 107A and the second support 107B are spaced apart on the system support 108, as the example shown in the perspective view and the lateral view in FIG. 3B.

Figure 4A:
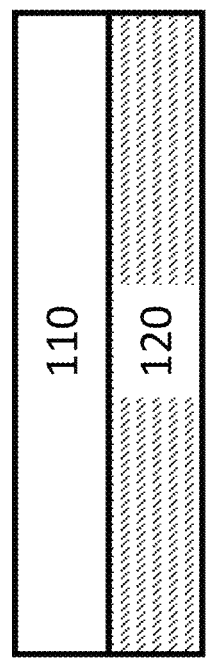
FIG. 4A-FIG. 4B each schematically show a cross-sectional view of the X-ray detector, according to an embodiment.

FIG. 4A schematically shows a cross-sectional view of one X-ray detector 100 of the first image sensor 101, according to an embodiment. The X-ray detector 100 of the first image sensor 101 may include an X-ray absorption layer 110 and an electronics layer 120 (e.g., an ASIC) for processing or analyzing electrical signals incident X-ray generates in the X-ray absorption layer 110. The X-ray absorption layer 110 may be configured to absorb the characteristic X-rays of the chemical element, and may include a semiconductor material such as GaAs. The semiconductor may have a high mass attenuation coefficient for the characteristic X-rays.

Figure 4B:
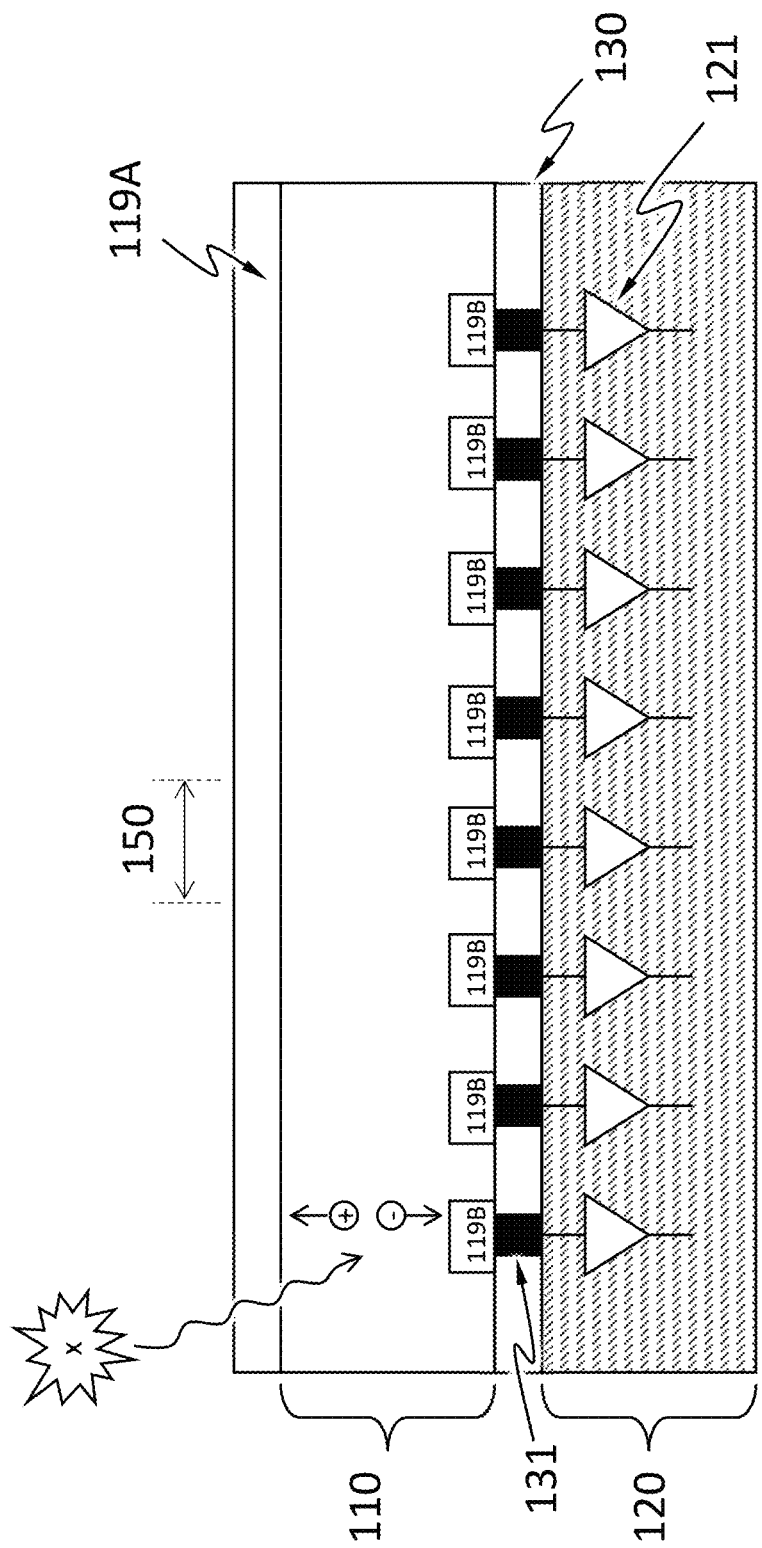

As shown in a detailed cross-sectional view of the X-ray detector 100 of the first image sensor 101 in FIG. 4B, according to an embodiment, the X-ray absorption layer 110 may include a resistor of a semiconductor material such as gallium arsenide (GaAs). The semiconductor may have a high mass attenuation coefficient for the characteristic X-rays.

When an X-ray photon hits the X-ray absorption layer 110 including a resistor, it may be absorbed and generate one or more charge carriers by a number of mechanisms. An X-ray photon may generate 10 to 100000 charge carriers. The charge carriers may drift to the electric contacts 119A and 119B under an electric field. The field may be an external electric field. The electric contact 119B includes discrete portions.

The electronics layer 120 may include an electronic system 121, suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 5:
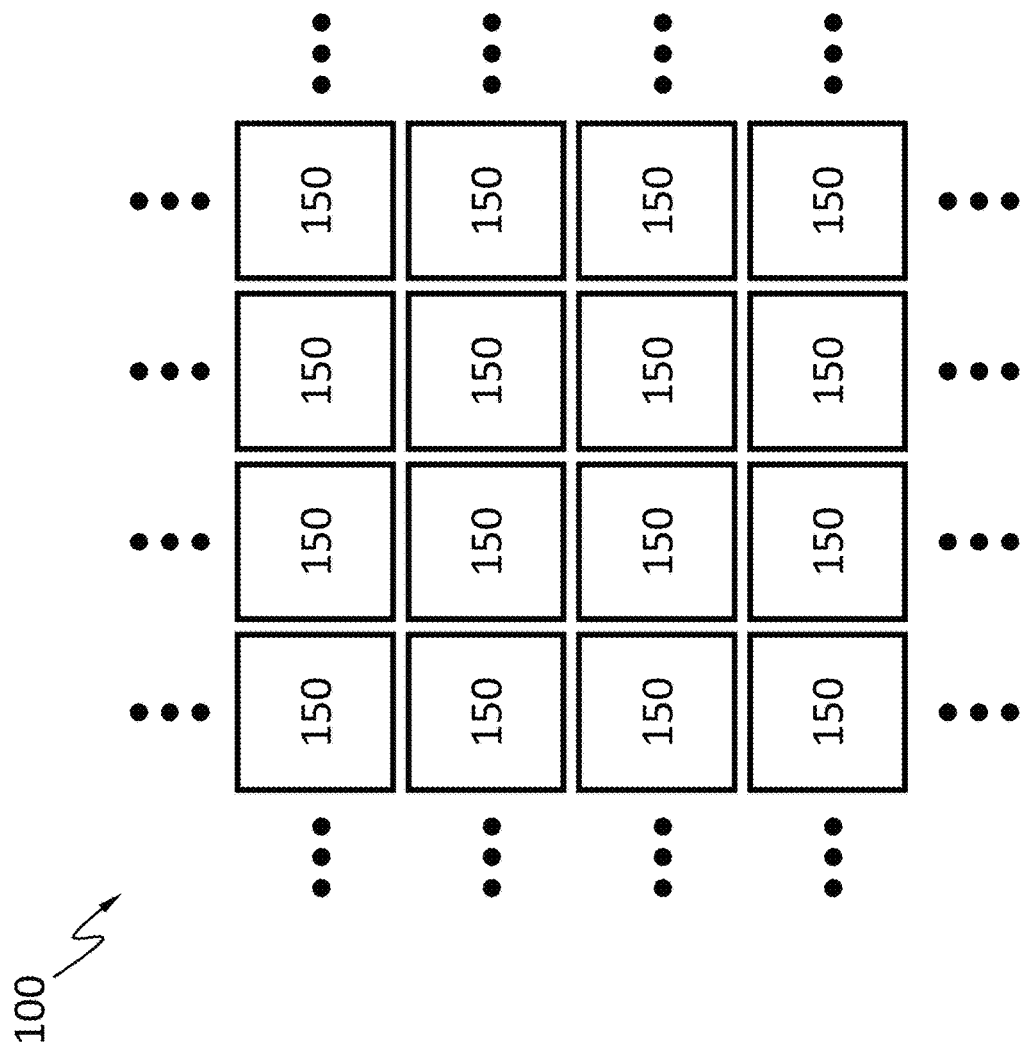
FIG. 5 schematically shows a top view of the X-ray detector, according to an embodiment.

FIG. 5 schematically shows a top view of the X-ray detector 100 included in the first image sensor 101, according to an embodiment. The X-ray detector 100 of the first image sensor 101 may have an array of pixels 150. The array may be a rectangular array, a honeycomb array, a hexagonal array or any other suitable array. Each pixel 150 is configured to count numbers of photons of the characteristic X-rays (e.g., the characteristic X-rays of the chemical element in the human breast tissues 104) incident on the pixels 150 within a period of time. The pixels 150 may be configured to operate in parallel. For example, when one pixel 150 measures an incident X-ray photon, another pixel 150 may be waiting for an X-ray photon to arrive. The pixels 150 may not have to be individually addressable. Each pixel 150 of the first image sensor 101 may be configured to count the numbers of X-ray photons within the same period of time. Therefore, capturing the images of the human breast tissues 104 comprises counting numbers of photons of the characteristic X-rays within a period of time. Each pixel 150 may be able to measure its dark current, such as before or concurrently with receiving each X-ray photon. Each pixel 150 may be configured to deduct the contribution of the dark current from the energy of the X-ray photon incident thereon.

Figure 6A:
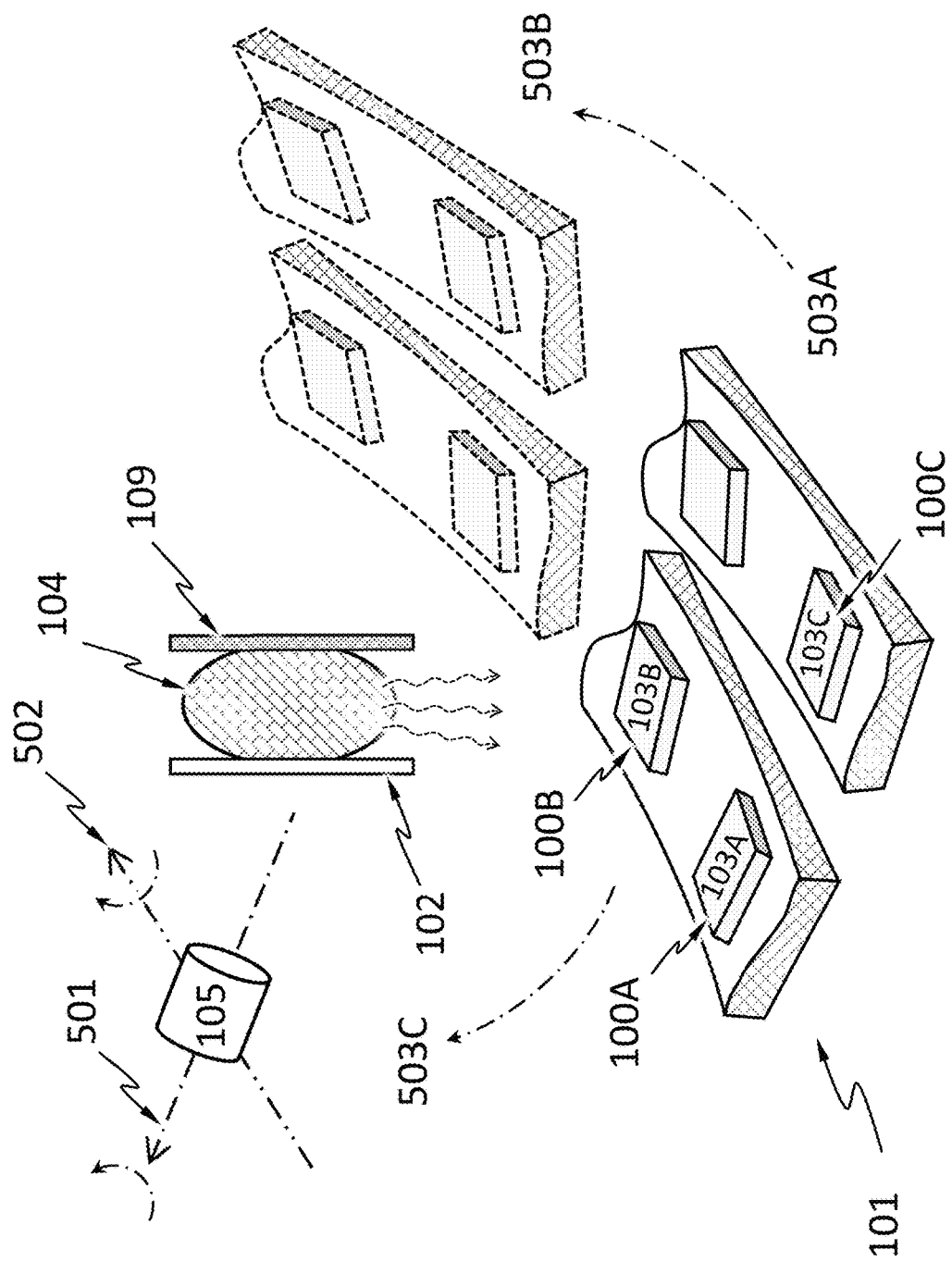
FIG. 6A and FIG. 6B schematically show movements of the first image sensor relative to a radiation source, according to an embodiment.
Figure 6B:
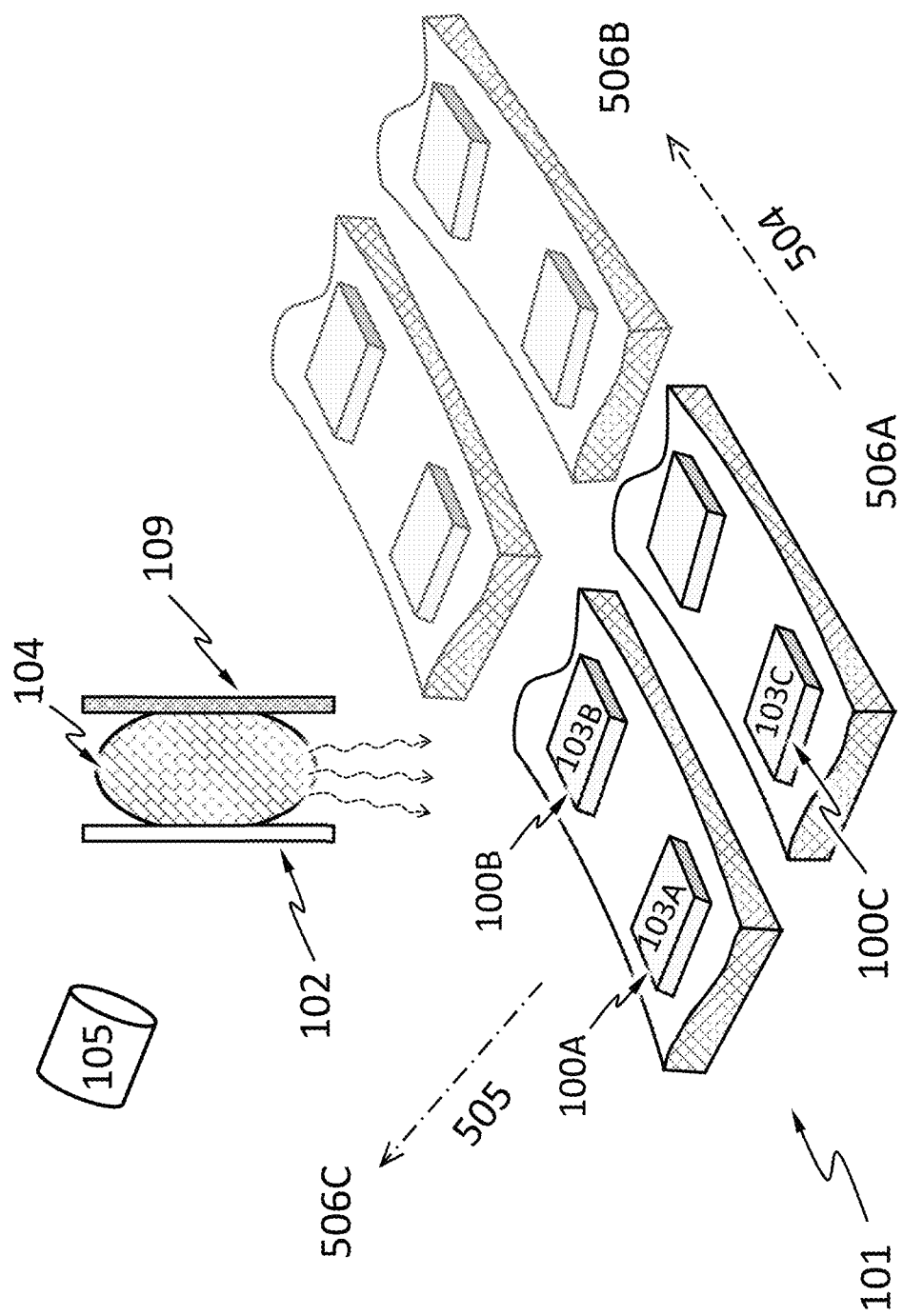

FIG. 6A and FIG. 6B schematically show movements of the first image sensor 101 comprising X-ray detectors 100 (e.g., 100A, 100B, 100C) relative to the radiation source 105, according to an embodiment. For brevity, in the examples of FIG. 6A and FIG. 6B, only a portion of the first image sensor 101 comprising multiple X-ray detectors 100 (e.g., 100A, 100B, 100C in FIG. 6A and FIG. 6B), the radiation source 105, and the human breast tissues 104 compressed between the clamp 109 are shown. The first image sensor 101 may be configured to rotate about a first axis 501 relative to the radiation source 105. As shown in the example of FIG. 6A, the first image sensor 101 rotates from position 503A to position 503B about the first axis 501, relative to radiation source 105. The first axis 501 may be parallel to the first planar surface 103A of the first X-ray detector 100A and the second planar surface 103B of the second X-ray detector 100B. The radiation source 105 may be on the first axis 501. The first image sensor 101 may be configured to rotate about a second axis 502 relative to the radiation source 105. The second axis 502 is different from the first axis 501. For example, the second axis 502 may be perpendicular to the first axis 501. As shown in the example of FIG. 6A, the first image sensor 101 rotate from position 503A to position 503C, about the second axis 502. The radiation source 105 may be on the second axis 502.

As shown in the example of FIG. 6B, the first image sensor 101 comprising the first X-ray detector 100A, the second X-ray detector 100B and the third X-ray detector 100C may be configured to translate along a first direction 504 from position 506A to position 506B, relative to the radiation source 105. As shown in the example of FIG. 6B, the first image sensor 101 may be configured to translate along a second direction 505 relative to the radiation source 105, from position 506A to position 506C. The second direction 505 may be different from the first direction 504. For example, the second direction 505 may be perpendicular to the first direction 504. In one embodiment, the first direction 504 is parallel to the first planar surface 103A, but not parallel to the second planar surface 103B. The second direction 505 may be parallel to both, either or neither of the first planar surface 103A of the first X-ray detector 100A and the second planar surface 103B of the second X-ray detector 100B.

FIG. 7A and FIG. 7B schematically show an example of movements of the first image sensor 101, the second image sensor 102 and the radiation source 105 relative to the human breast tissues 104, according to an embodiment. In the example shown in FIG. 7A, at time to, the radiation source 105 is at a first position 602A, the second image sensor 102 is configured to receive radiations from the radiation source 105 that transmit through the human breast tissues 104, and the first image sensor 101 is between the radiation source 105 and the second image sensor 102, receiving excited characteristic X-ray from the human breast tissues 104. At time $t_1$, the first image sensor 101, the second image sensor 102 and the radiation source 105 may collectively rotate to a second position 602B, relative to the human breast tissues 104 about one or more axes, e.g., an axis 601. Namely, the first image sensor 101, the second image sensor 102 and the radiation source 105 may collectively rotate relative to the human breast tissues 104 about the axis 601. At least one or more axes, e.g., the axis 601, may be on the human breast tissues 104. According to one embodiment, the first position 603A and the second position 603B are different.

FIG. 7C and FIG. 7D schematically show an example of movement of the radiation source 105 relative to the human breast tissues 104, according to an embodiment. In the example shown in FIG. 7C, at time $t_2$, the radiation source 105 is at the first position 602A, the second image sensor 102 is configured to receive radiations from the radiation source 105 that transmit through the human breast tissues 104, and the first image sensor 101 is between the radiation source 105 and the second image sensor 102, receiving excited characteristic X-ray from the human breast tissues 104. At time $t_3$, the radiation source 105 may rotate to a third position 602C, relative to the human breast tissues 104 about one or more axes, e.g., the axis 601. Namely, the radiation source 105 may rotate relative to the human breast tissues 104 about the axis 601. The axis 601 may be on the human breast tissues 104. The first image sensor 101 and the second image sensor 102 may remain stationary relative to the human breast tissues 104, during and after the rotation of the radiation source 105. According to one embodiment, the first position 602A, the second position 602B, the third position 602C are different.

Figure 8B:
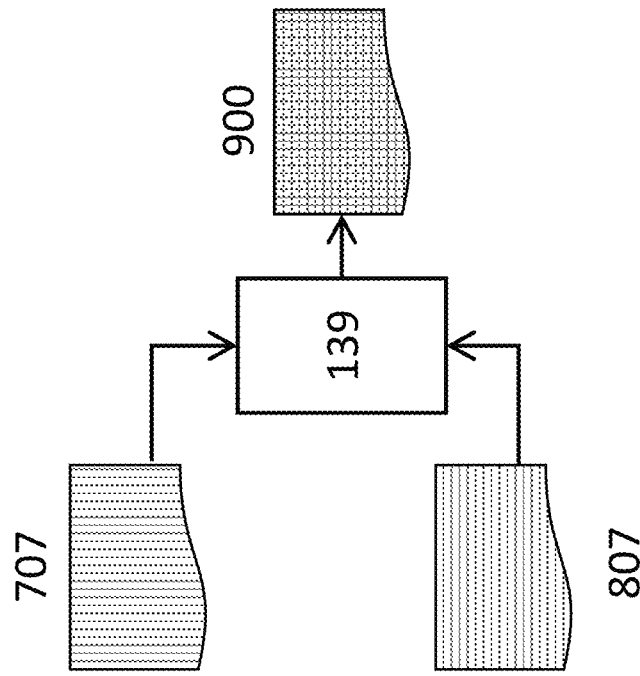
FIG. 8B schematically shows an example of superposing the three-dimensional distribution of the chemical element and the three-dimensional image of the human breast tissues by a processor, according an embodiment.
Figure 8A:
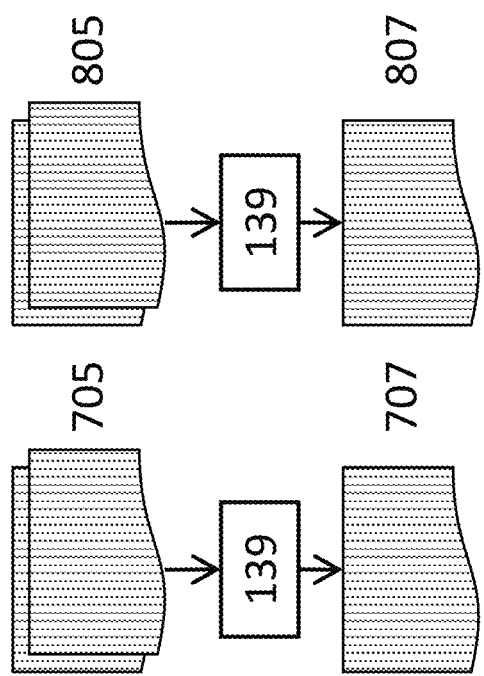
FIG. 8A schematically shows examples of a three-dimensional distribution of the chemical element determined based on a first set of images, and a three-dimensional image of the human breast tissues reconstructed based on a second set of images, according an embodiment.

FIG. 8A schematically shows an example where a three-dimensional distribution 707 of the chemical element is determined based on the first set of images 705, and a three-dimensional image 807 of the human breast tissues 104 reconstructed based on the second set of images 805, for example using the processor 139, according to an embodiment. Various algorithms may be applied to determine the three-dimensional distribution 707. Various suitable reconstruction algorithms may be applied to reconstruct the three-dimensional image 807 of the human breast tissues 104.

FIG. 8B schematically shows an example of superposing the three-dimensional distribution 707 of the chemical element and the three-dimensional image 807 of the human breast tissues 104 by the processor 139, according an embodiment. In the example of FIG. 8B, the processor 139 is configured to superpose the three-dimensional distribution of the chemical element (e.g., 707) with the three-dimensional image of the human breast tissues (e.g., 807) to form a superposed image 900, which has chemical element distribution information is integrated in the three-dimensional image of the human breast tissues 104. Various suitable superposing algorithms may be applied.

Figure 9:
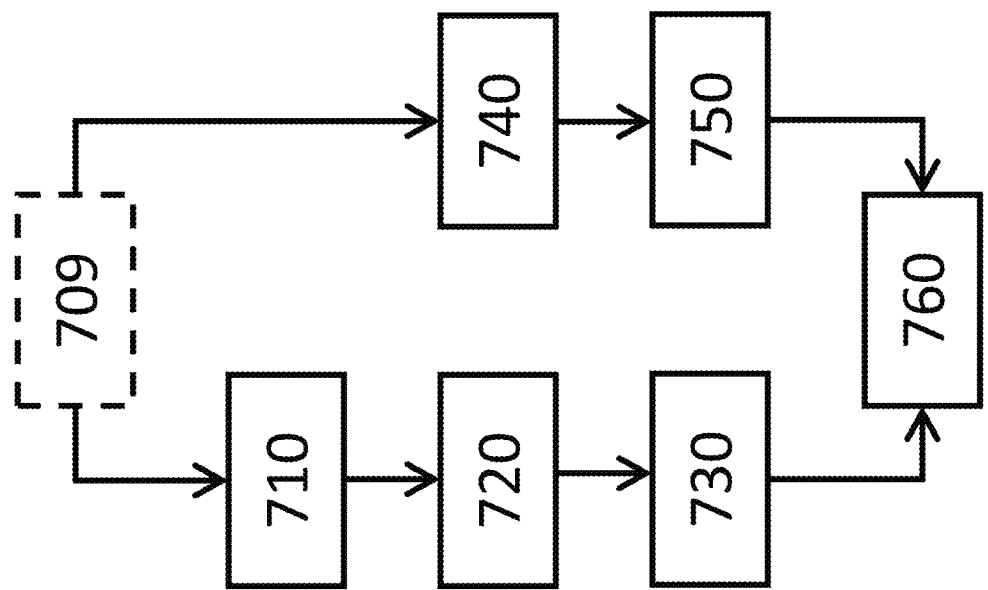
FIG. 9 shows flowchart for a method, according to an embodiment.

FIG. 9 shows a flowchart for a method, according to an embodiment. In optional procedure 709, a chemical element may be introduced into the human breast tissues 104 orally by pills or liquids, or by injection into bloodstreams. The chemical element may be a non-radioactive chemical element. The chemical element may be bound to a ligand. Examples of the chemical element may include rhenium or iodine. In procedure 710, emission of the characteristic X-rays of the chemical element in the human breast tissues 104 is caused, for example, by irradiating the human breast tissues 104 with radiation from a radiation source 105. In procedure 720, a first set of images are captured with the only characteristic X-rays of the chemical element in human breast tissues 104. The images may be captured respectively at multiple positions relative to the human breast tissues 104 using a first image sensor 101. In procedure 730, a three-dimensional distribution of the chemical element in the human breast tissues 104 is determined by a processor 139 based on the first set of images. In procedure 740, a second set of images of the human breast tissues 104 are captured with the radiation from the radiation source transmitted through of the human breast tissues 104. The images may be captured respectively at multiple positions using a second image sensor 102. In procedure 750, a three-dimensional image of the human breast tissues 104 is reconstructed by the processor 139 based on the second set of images. In procedure 760, the three-dimensional distribution of the chemical element and the three-dimensional image are superposed by the processor 139.

Figure 10A:
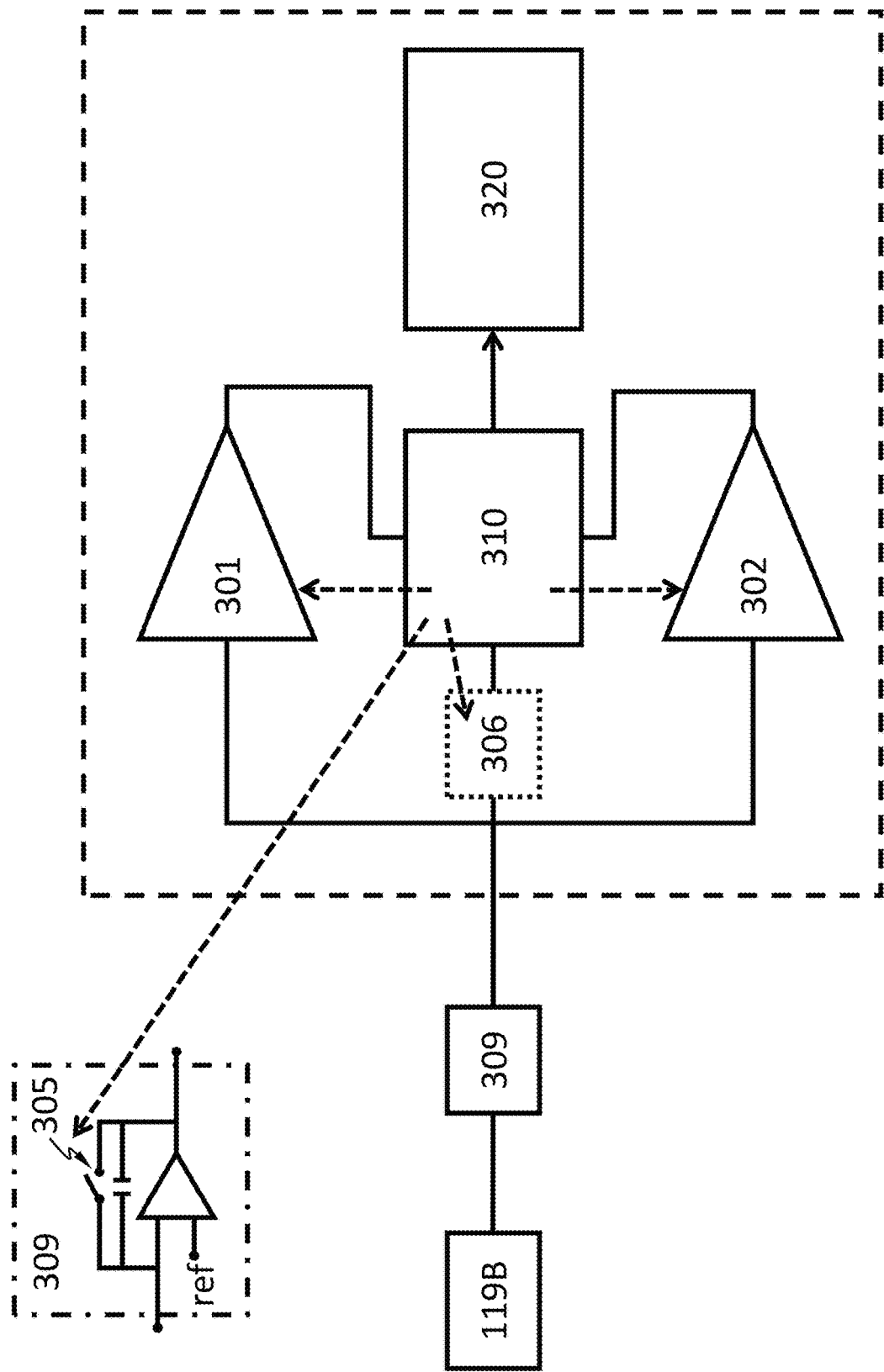
FIG. 10A-FIG. 10B each schematically show a component diagram of an electronic system, according to an embodiment.
Figure 10B:
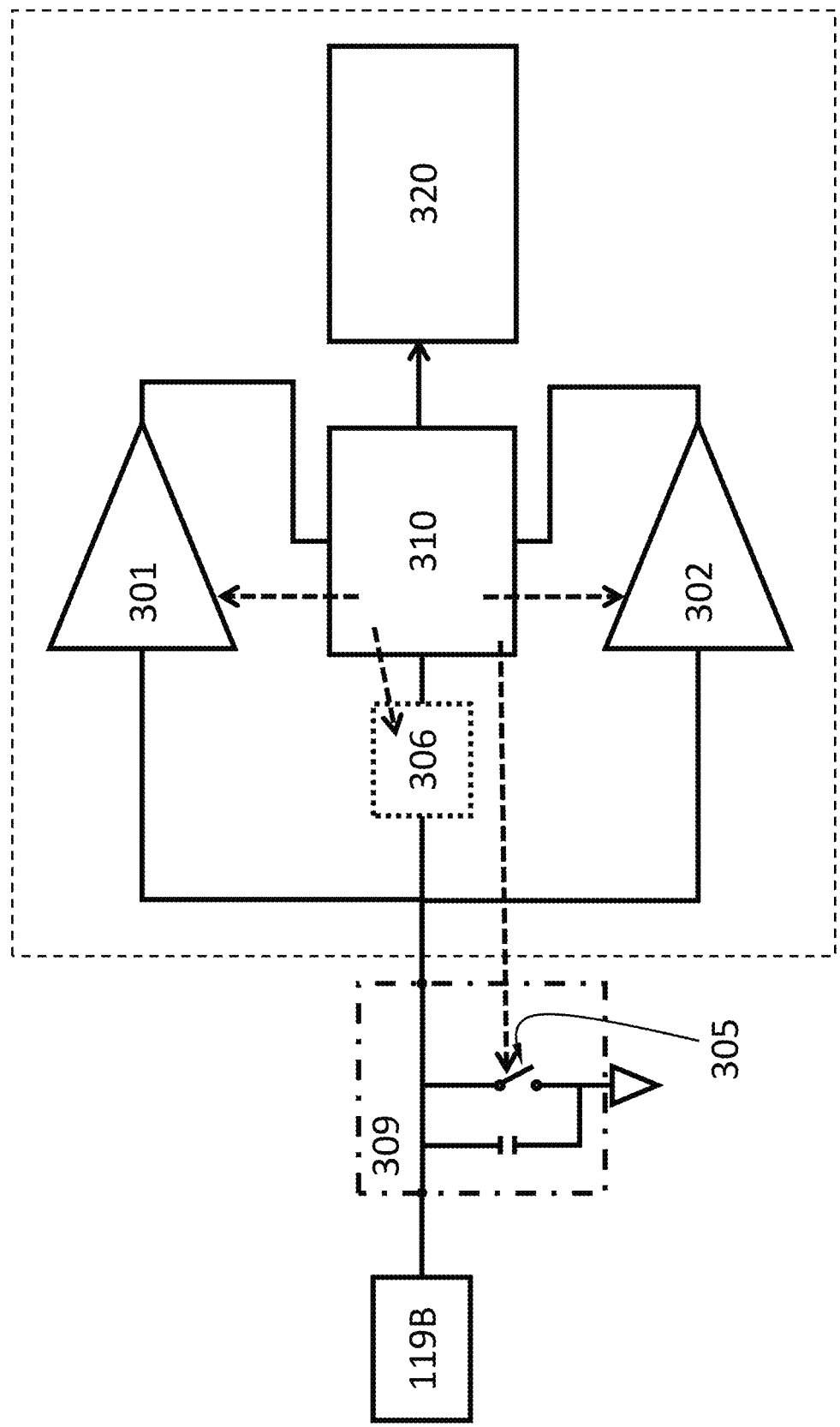

FIG. 10A and FIG. 10B each show a component diagram of the electronic system 121, according to an embodiment. The electronic system 121 may include a first voltage comparator 301, a second voltage comparator 302, a counter 320, a switch 305, an optional voltmeter 306 and a controller 310.

The first voltage comparator 301 is configured to compare the voltage of at least one of the electric contacts 119B to a first threshold. The first voltage comparator 301 may be configured to monitor the voltage directly, or to calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident photon of X-ray may generate on the electric contact 119B. The maximum voltage may depend on the energy of the incident photon of X-ray, the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident photon of X-ray may generate on the electric contact 119B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident photons of X-rays. However, having a high speed is often at the cost of power consumption.

The counter 320 is configured to register at least a number of photons of X-rays incident on the pixel 150 encompassing the electric contact 119B. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phrase "the rate of change of the voltage is substantially zero" means that temporal change of the voltage is less than 0.1%/ns. The phrase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 11:
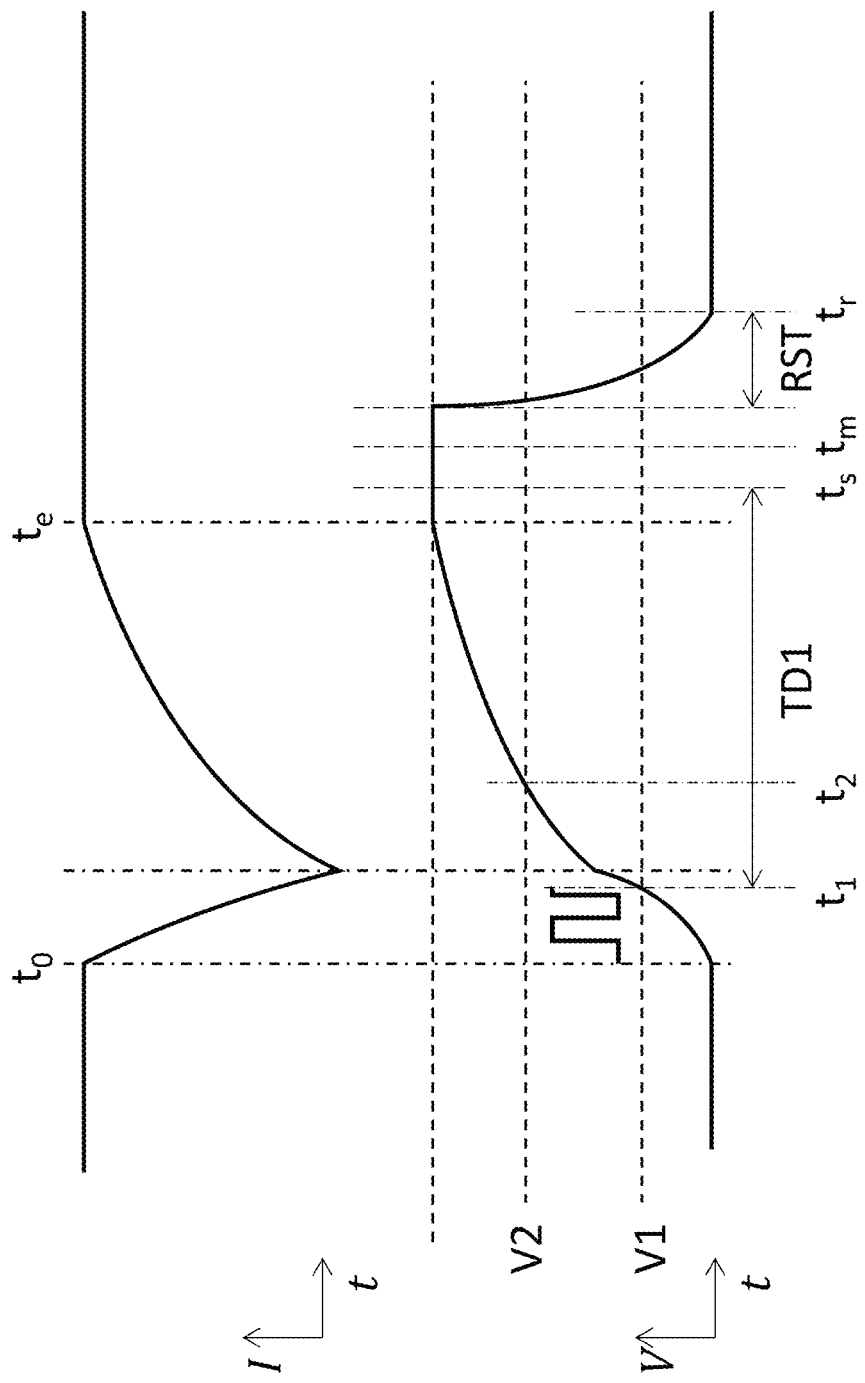
FIG. 11 schematically shows a temporal change of an electric current caused by charge carriers generated by an incident photon of X-ray, and a corresponding temporal change of a voltage, according to an embodiment.

FIG. 11 schematically shows a temporal change of the electric current flowing through the electric contact 119B (upper curve) caused by charge carriers generated by a photon of X-ray incident on the pixel 150 encompassing the electric contact 119B, and a corresponding temporal change of the voltage of the electric contact 119B (lower curve). The voltage may be an integral of the electric current with respect to time. At time $t_0$, the photon of X-ray hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the photon of X-ray drift out of the X-ray absorption layer 110. At time $t_s$, the time delay TD1 expires. At or after time $t_e$, the controller 310 causes the voltmeter 306 to digitize the voltage and determines which bin the energy of the photon of X-ray falls in. The controller 310 then causes the number registered by the counter 320 corresponding to the bin to increase by one. In the example of FIG. 11, time $t_s$ is after time $t_e$; namely TD1 expires after all charge carriers generated by the photon of X-ray drift out of the X-ray absorption layer 110. If time $t_e$ cannot be easily measured, TD1 can be empirically chosen to allow sufficient time to collect essentially all charge carriers generated by a photon of X-ray but not too long to risk have another incident photon of X-ray. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the photon of X-ray, which relates to the energy of the photon of X-ray. The controller 310 may be configured to determine the energy of the photon of X-ray, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the electronic system 121 is ready to detect another incident photon of X-ray. If the first voltage comparator 301 has been deactivated, the controller 310 can activate it at any time before RST expires. If the controller 310 has been deactivated, it may be activated before RST expires.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   a radiation source configured to cause emission of characteristic X-rays of a chemical element in human breast tissues by generating and directing radiation to the human breast tissues;
   a first image sensor configured to capture a first set of images of the human breast tissues using the characteristic X-rays;
   a second image sensor configured to capture a second set of images of the human breast tissues using the radiation that has transmitted through the human breast tissues; and
   a clamp configured to compress the human breast tissues against the second image sensor;
   wherein the first image sensor is between the clamp and the second image sensor.

2. The system of claim 1, wherein the radiation source comprises a filter configured to block radiation not having sufficient energy to cause the emission of the characteristic X-rays.

3. The system of claim 1, wherein the chemical element is rhenium or iodine.

4. The system of claim 1, wherein the chemical element is not radioactive.

5. The system of claim 1, wherein the chemical element is bound to a ligand.

6. The system of claim 1, wherein the first image sensor comprises an array of pixels, and is configured to count numbers of photons of the characteristic X-rays incident on the pixels within a period of time.

7. The system of claim 1, wherein the first image sensor comprises an X-ray absorption layer comprising GaAs.

8. The system of claim 1, wherein the first image sensor does not comprise a scintillator.

9. The system of claim 1, wherein the first set of images are captured using only the characteristic X-rays.

10. The system of claim 1, further comprising a processor configured to determine a three-dimensional distribution of the chemical element, based on the first set of images.

11. The system of claim 10, wherein the processor is configured to reconstruct a three-dimensional image of the human breast tissues based on the second set of images.

12. The system of claim 11, wherein the processor is configured to superposing the three-dimensional distribution of the chemical element and the three-dimensional image.

13. The system of claim 1, wherein the first image sensor is configured to move between a first position relative to the radiation source and a second position relative to the radiation source.

14. The system of claim 1, wherein the first image sensor, the second image sensor and the radiation source are configured to collectively rotate relative to the human breast tissues.

15. The system of claim 1, wherein the radiation source is configured to rotate relative to the human breast tissues while the first image sensor and the second image sensor remain stationary relative to the human breast tissues.

16. A method, comprising:
   causing emission of characteristic X-rays of a chemical element in human breast tissues by directing radiation to the human breast tissues;
   capturing a first set of images of the human breast tissues using the characteristic X-rays using a first image sensor;
   capturing a second set of images of the human breast tissues using the radiation that has transmitted through the human breast tissues using a second image sensor;
   determining a three-dimensional distribution of the chemical element in the human breast tissues based on the first set of images;
   reconstructing a three-dimensional image of the human breast tissues based on the second set of images;
   superposing the three-dimensional distribution of the chemical element and the three-dimensional image;
   wherein the human breast tissues are compressed by a clamp against the second image sensor;
   wherein the first image sensor is between the clamp and the second image sensor.

17. The method of claim 16, wherein the chemical element is rhenium or iodine.

18. The method of claim 16, wherein the chemical element is not radioactive.

19. The method of claim 16, wherein the chemical element is bound to a ligand.

20. The method of claim 16, wherein the first image sensor comprises an array of pixels, and is configured to count numbers of photons of the characteristic X-rays incident on the pixels within a period of time.

21. The method of claim 16, wherein capturing the first set of images are captured using only the characteristic X-rays.

22. The method of claim 16, wherein the first image sensor and the second image sensor remain stationary relative to the human breast tissues during capturing the first set of images and capturing the second set of images.

* * * * *